United States Patent
Wegrzyn, III et al.

(10) Patent No.: US 7,561,917 B2
(45) Date of Patent: Jul. 14, 2009

(54) FEEDTHROUGH ASSEMBLY INCLUDING SLEEVE AND METHODS RELATED THERETO

(75) Inventors: Thomas J. Wegrzyn, III, Lauderdale, MN (US); Edward J. Maierhofer, Brooklyn Park, MN (US); James P. Rohl, Prescott, WI (US); Stephen W. VanDerlick, Andover, MN (US); Benjamin J. Haasl, Forest Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 146 days.

(21) Appl. No.: 11/277,213

(22) Filed: Mar. 22, 2006

(65) Prior Publication Data

US 2007/0225771 A1    Sep. 27, 2007

(51) Int. Cl.
*A61N 1/39* (2006.01)
(52) U.S. Cl. ............................. 607/36; 607/37; 385/138
(58) Field of Classification Search ................... 607/36, 607/37; 385/138
See application file for complete search history.

(56) References Cited

U.S. PATENT DOCUMENTS

| | | | |
|---|---|---|---|
| 1,482,288 A | | 1/1924 | Deuscher |
| 4,678,868 A | * | 7/1987 | Kraska et al. ......... 174/152 GM |
| 4,963,101 A | * | 10/1990 | Lee ............................. 439/266 |
| 5,144,946 A | * | 9/1992 | Weinberg et al. .............. 607/2 |
| 5,489,225 A | * | 2/1996 | Julian .......................... 439/837 |
| 5,571,146 A | * | 11/1996 | Jones et al. ................... 607/37 |
| 5,782,891 A | * | 7/1998 | Hassler et al. ................ 607/36 |
| 5,817,984 A | | 10/1998 | Taylor et al. |
| 5,866,851 A | | 2/1999 | Taylor et al. |
| 5,871,513 A | | 2/1999 | Taylor et al. |
| 5,926,357 A | * | 7/1999 | Elias et al. ................... 361/302 |

(Continued)

FOREIGN PATENT DOCUMENTS

DE          856473          11/1952

(Continued)

OTHER PUBLICATIONS

PCT Application No. PCT/US2007/064367 International Search Report mailed Dec. 14, 2007, 4 pgs.

(Continued)

*Primary Examiner*—Mark W Bockelman
*Assistant Examiner*—Roland Dinga
(74) *Attorney, Agent, or Firm*—Schwegman, Lundberg & Woessner, P.A.

(57) ABSTRACT

A feedthrough assembly is disposable in an aperture of, for example, a power source encasement. In various examples, the feedthrough assembly comprises a ferrule, an insulator, a terminal conductor, and a sleeve. A portion of the terminal conductor extends through the ferrule thereby creating a portion internal to and a portion external to the encasement. The insulator is disposed within the ferrule and is sealably engaged with the terminal conductor portion extending through the ferrule. The sleeve is disposed over the internal portion of the terminal conductor and coupled thereto. In one example, the sleeve includes at least one notch on a sleeve first end or a sleeve second end, which may be used to weld or solder the sleeve to the terminal conductor. In another example, the sleeve includes a longitudinally extending void, which may be used to crimp the sleeve to the terminal conductor.

27 Claims, 8 Drawing Sheets

U.S. PATENT DOCUMENTS

| | | | |
|---|---|---|---|
| 6,042,624 A * | 3/2000 | Breyen et al. | 29/25.03 |
| 6,080,188 A * | 6/2000 | Rowley et al. | 607/37 |
| 6,191,931 B1 * | 2/2001 | Paspa et al. | 361/302 |
| 6,366,820 B1 * | 4/2002 | Doan et al. | 607/122 |
| 6,498,951 B1 * | 12/2002 | Larson et al. | 607/36 |
| 6,671,187 B1 * | 12/2003 | Zayatz | 361/824 |
| 6,801,424 B1 * | 10/2004 | Nielsen et al. | 361/517 |
| 6,812,404 B1 | 11/2004 | Martinez | |
| 2004/0258988 A1 | 12/2004 | Nielsen et al. | |
| 2004/0260354 A1 * | 12/2004 | Nielsen et al. | 607/37 |
| 2005/0060003 A1 * | 3/2005 | Taylor et al. | 607/36 |

FOREIGN PATENT DOCUMENTS

| | | |
|---|---|---|
| EP | 1632265 A1 | 3/2006 |
| GB | 578704 | 7/1946 |
| GB | 1176311 | 1/1970 |

OTHER PUBLICATIONS

PCT Application No. PCT/US2007/064367 Written Opinion mailed Dec. 14, 2007, 7 pgs.

* cited by examiner

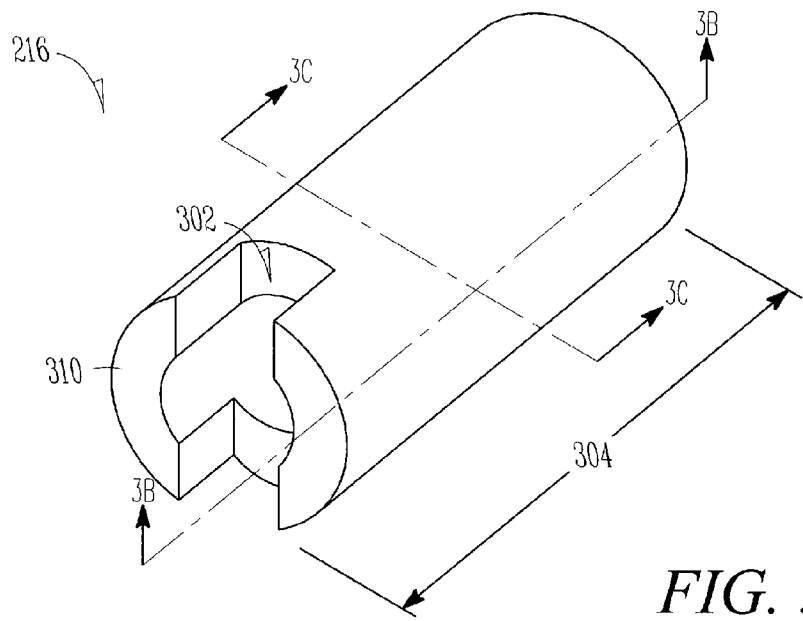
*FIG. 3A*
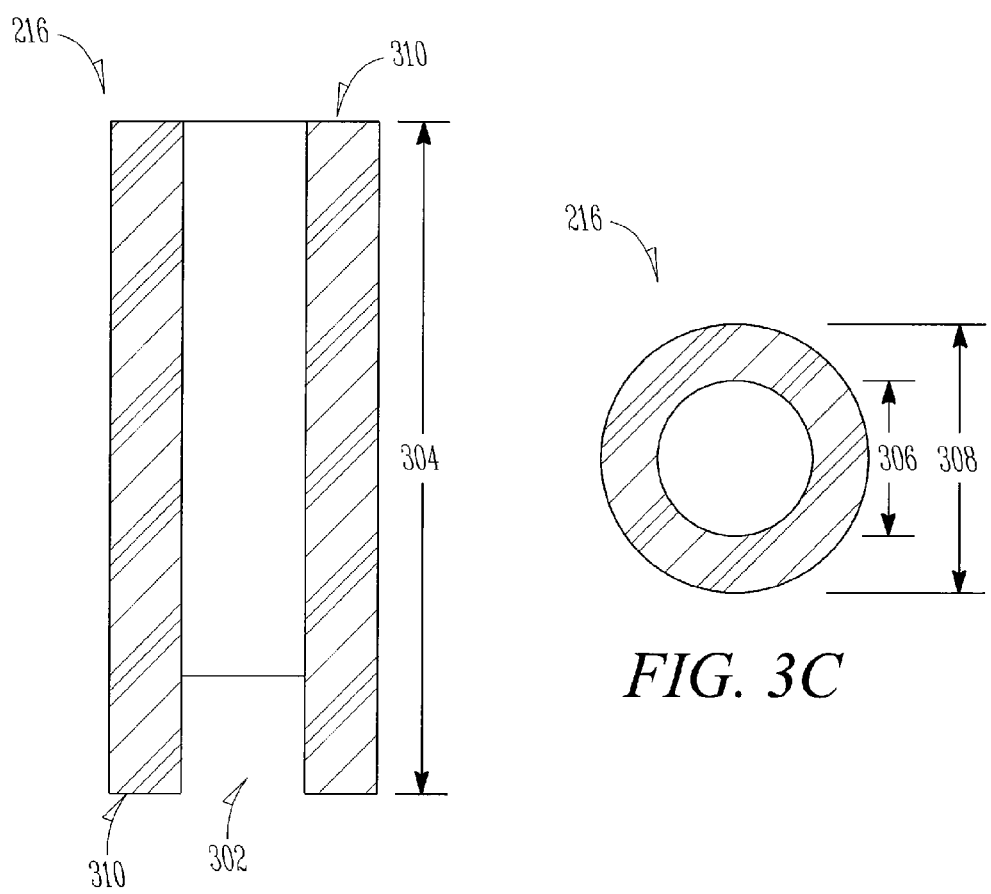
*FIG. 3B*
*FIG. 3C*

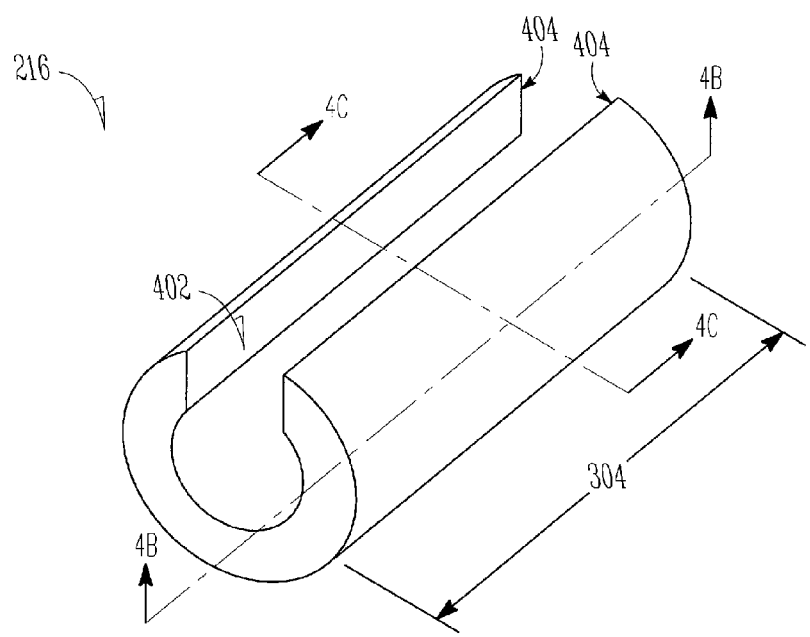
*FIG. 4A*
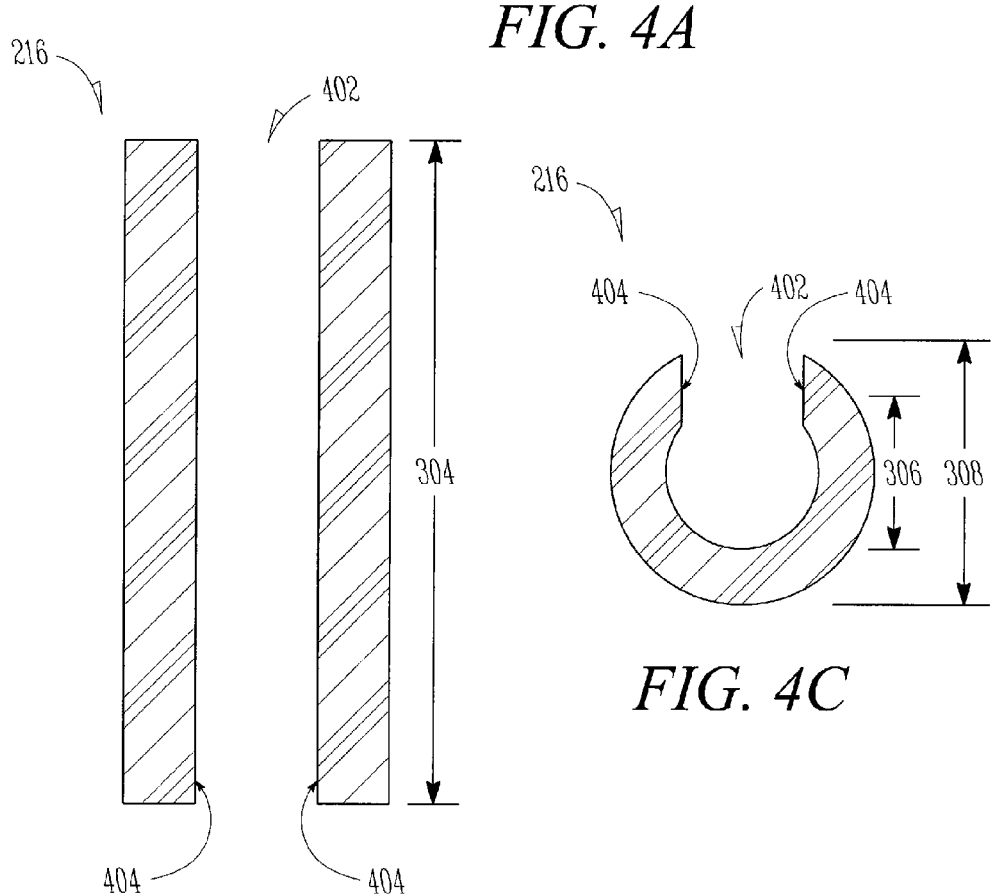
*FIG. 4B*
*FIG. 4C*

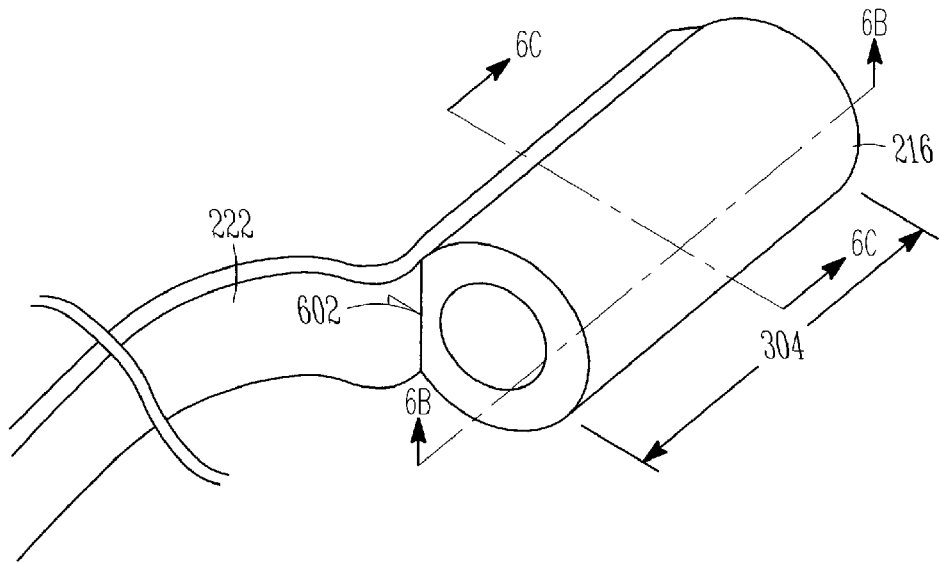
FIG. 6A
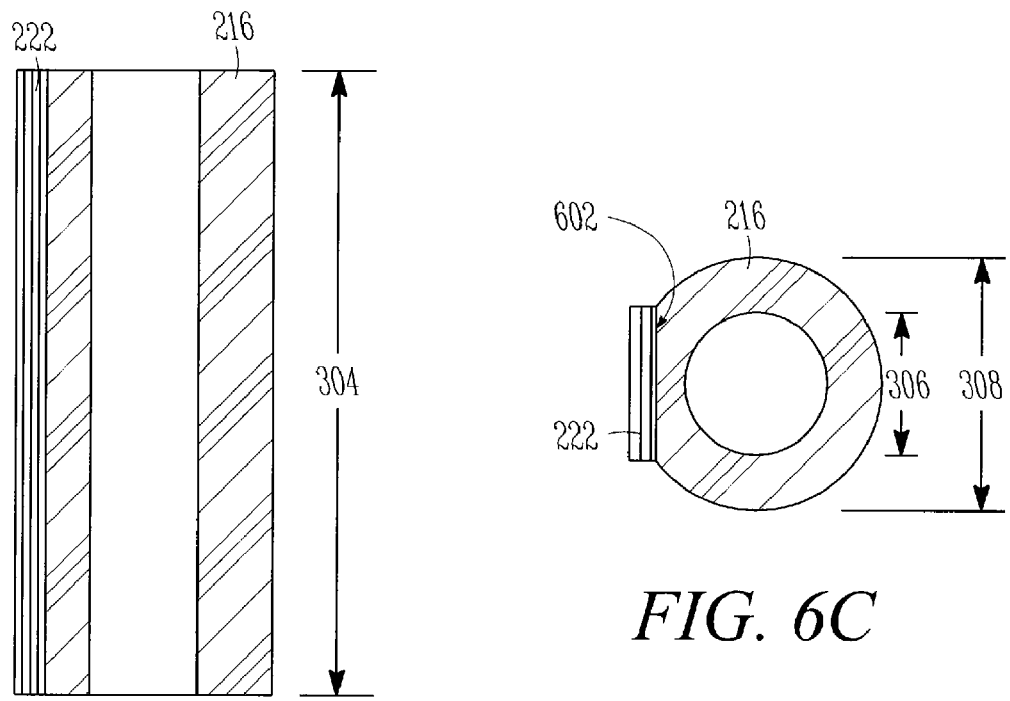
FIG. 6C
FIG. 6B

:

FEEDTHROUGH ASSEMBLY INCLUDING SLEEVE AND METHODS RELATED THERETO

TECHNICAL FIELD

This patent document pertains generally to electrical feedthrough assemblies for use in medical devices, and more particularly, but not by way of limitation, to feedthrough assemblies including a sleeve and methods related thereto.

BACKGROUND

Numerous applications involve penetrating a sealed encasement (i.e., a container) so-as-to provide electrical access to or from electrical components enclosed within. One such application involves body implantable medical devices (referred to as "IMDs"), such as pulse generators or cardiac function management devices, for the treatment of bradycardia, tachyarrhythmia, or muscle or nerve stimulation. One such example involves providing electrical access to and from a power source (e.g., a battery) of an IMD.

Electrical feedthrough assemblies provide a conductive path extending between the interior of the (hermetically sealed) encasement and a location outside the encasement. Typically, the conductive path comprises a conductive pin or other type of terminal that is electrically insulated from the encasement. In addition, feedthrough assemblies may include a ferrule and an insulative material for positioning and insulating the pin within the ferrule. In the battery power source example, a conductive connection member is often directly coupled to an internal portion (i.e., a portion located within the battery encasement) of the conductive pin on a first end and coupled to an anode or cathode (of the battery) on a second end.

When used in IMDs, feedthrough assemblies need to provide years of reliable service since maintenance or repair possibilities for the devices are extremely limited or costly. Moreover, failures of the feedthrough assembly or components thereof can have catastrophic consequences as extreme as death for a patient reliant on the IMD. Therefore, feedthrough assemblies need to comprise, among other things, highly reliable components and secure interconnections.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

FIG. 3A illustrates an isometric view of a sleeve for use in a feedthrough assembly.

FIG. 3B illustrates a cross-sectional view of the sleeve of FIG. 3A along line 3B-3B.

FIG. 3C illustrates a cross-sectional view of the sleeve of FIG. 3A along line 3C-3C.

FIG. 4A illustrates an isometric view of another sleeve for use in a feedthrough assembly.

FIG. 4B illustrates a cross-sectional view of the sleeve of FIG. 4A along line 4B-4B.

FIG. 4C illustrates a cross-sectional view of the sleeve of FIG. 4A along line 4C-4C.

FIG. 6A illustrates an isometric view of another sleeve for use in a feedthrough assembly and a portion of a conductive connection member coupled therewith.

FIG. 6B illustrates a cross-sectional view of the sleeve of FIG. 6A along line 6B-6B.

FIG. 6C illustrates a cross-sectional view of the sleeve of FIG. 6A along line 6C-6C.

DETAILED DESCRIPTION

The following detailed description includes references to the accompanying drawings, which form a part of the detailed description. The drawings show, by way of illustration, specific embodiments in which the present assemblies and methods may be practiced. These embodiments, which are also referred to herein as "examples," are described in enough detail to enable those skilled in the art to practice the present assemblies and methods. The embodiments may be combined, other embodiments may be utilized, or structural, logical and electrical changes may be made without departing from the scope of the present assemblies and methods. The following detailed description is, therefore, not to be taken in a limiting sense, and the scope of the present assemblies and methods are defined by the appended claims and their legal equivalents.

In this document the terms "a" or "an" are used to include one or more than one; the term "or" is used to refer to a nonexclusive or unless otherwise indicated; and the term "subject" is used to include the term "patient." In addition, it is to be understood that the phraseology or terminology employed herein, and not otherwise defined, is for the purpose of description only and not of limitation.

Introduction

The present assemblies and methods provide, among other things, a conductive path extending between the interior of an encasement, such as an IMD power source encasement, and a location outside the encasement via a feedthrough assembly including a sleeve. Use of a sleeve increases the connection strength between components of the feedthrough assembly (e.g., a terminal conductor and a conductive connection member). This enhances the reliability of the feedthrough assembly and IMDs employing the same. In addition, a sleeve facilitates manufacturability of feedthrough assembly connections (e.g., by providing a larger connection surface area for welding, soldering, or brazing a conductive connection member to a terminal conductor) thereby reducing manufacturing costs. These and other aspects, advantages, and features of the present assemblies and methods will become apparent from a consideration of the following description and associated drawings.

EXAMPLES

Figure 1:
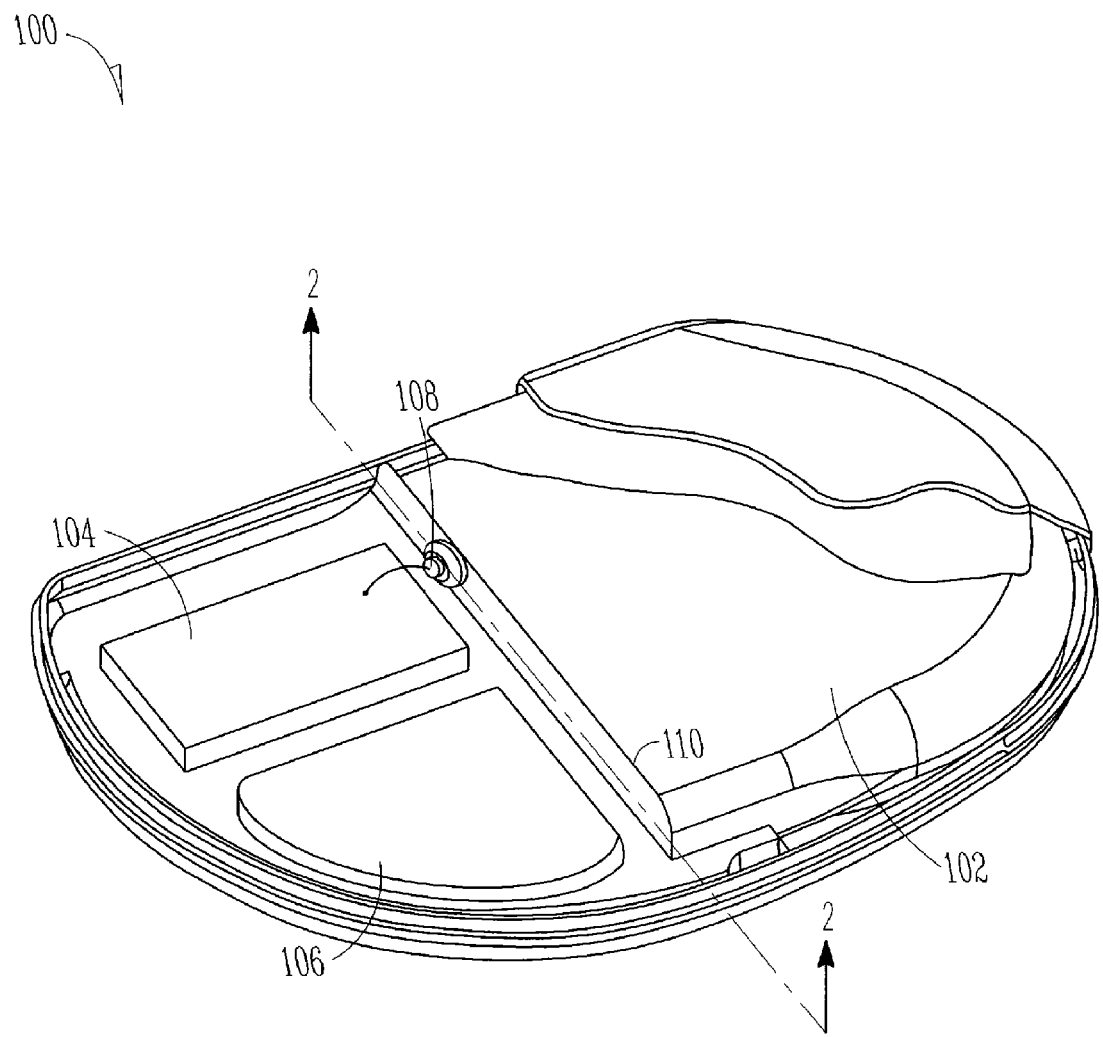
FIG. 1 illustrates a generalized isometric view of an implantable medical device.

In FIG. 1, an example of a generic IMD 100 is illustrated. In this example, IMD 100 includes a power source section 102, an electronics section 104, a capacitor section 106, and one or more feedthrough assemblies 108. The "IMD" will typically include, among other things, cardiac function management (referred to as "CFM") systems such as pacemakers, cardioverters/defibrillators, paces/defibrillators, biventricular or other multi-site resynchronization or coordination devices such as cardiac resynchronization therapy (referred to as "CRT") devices, or drug delivery systems.

Figure 2:
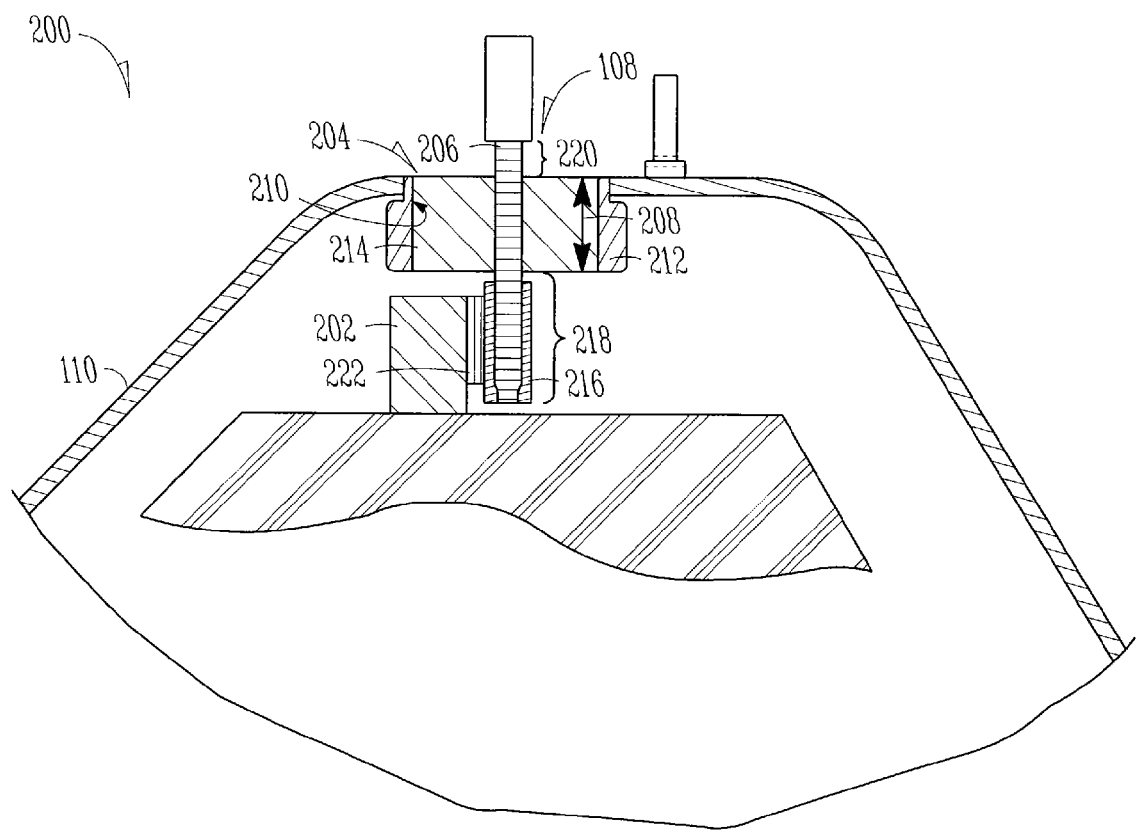
FIG. 2 illustrates a cross-sectional view of a feedthrough assembly and an encasement along line 2-2 of FIG. 1.

Power source section 102 may include, but is not limited to, an electrochemical cell, an electrolytic or other capacitor, or a battery. In one example, power source section 102 comprises a battery having an anode or a cathode 202 terminal (FIG. 2) and is enclosed by an encasement 110, such as a can or other container. In the example of FIG. 2, encasement 110 includes at least one encasement aperture 204 into which the one or more feedthrough assemblies 108 are mounted. As discussed above, feedthrough assembly 108 penetrates the otherwise sealed encasement 110, such as to provide electrical access to or from one or more electrical components (e.g., an anode or a cathode terminal 202) enclosed therewithin.

Notably, FIG. 1 illustrates one example of various sections and assemblies of an IMD 100. Power source section 102, electronics section 104, capacitor section 106, and the one or more feedthrough assemblies 108 are illustrated separately for conceptual clarity; however, such sections and assemblies may be further separated or need not be separately embodied.

FIG. 2 illustrates a cross-sectional view 200, such as along line 2-2 of FIG. 1, of an example of a single-terminal feedthrough assembly 108 and a (battery) encasement 110 into which feedthrough assembly 108 provides access to or from. In this example, encasement 110 includes at least one aperture 204 into which feedthrough assembly 108 is mounted. In various examples, feedthrough assembly 108 is coupled to a wall surface of aperture 204, such as via (laser or resistance) welding, soldering, brazing, gluing, or any other suitable connection technique known in the art.

In the example of FIG. 2, feedthrough assembly 108 includes a ferrule 212, an insulator member or body 214 contacting ferrule 212, a terminal conductor (e.g., a conductor pin) 206 with a length 208 portion extending through an opening 210 in ferrule 212, and a sleeve 216. By identifying a portion of its length 208 as extending through opening 210, terminal conductor 206 may be conceptualized as having an internal portion 218 extending into the interior of encasement 110 and an external portion 220 extending out of encasement 110. Using one or more of a variety of techniques, as further discussed below, sleeve 216 is affixed to internal portion 218 of terminal conductor 206, such as to increase the strength or reliability of one or more connections made thereto, such as by a conductive connection member 222.

In the example of FIG. 2, insulator member or body 214 surrounds at least a portion of the length 208 of the terminal conductor 206 extending through opening 210. In one example, insulator 214 comprises a glass such as sapphire; however, the present assemblies and methods are not so limited. Insulator member or body 214 can be made of any suitable ceramic-containing material or other electrically-insulative material such as diamond, ruby, zinc oxide, or even one or more high dielectric polymers such as one or more polyimides. Among other utilities, insulator member or body 214 prevents a short circuit from occurring between terminal conductor 206 and ferrule 212 or encasement 110.

In order to ensure a tight seal between insulator member or body 214 and the walls of encasement 110 or encasement aperture 204, ferrule 212 may be disposed as a (thin) sleeve therebetween. Among other things, ferrule 212 provides a support for insulator 214 and terminal conductor 206 or a means for mounting feedthrough assembly 108 in encasement 110, such as via welding, soldering, brazing, gluing, or any other suitable connection. Ferrule 212 is typically annular; however, ferrule 212 may have any other configuration suitable for use with encasement 110. Ferrule 212 may comprise any material or combination of materials known in the art to be suitable for providing support for insulator 214 and terminal conductor 206 or providing a means for mounting feedthrough assembly 108 in encasement 110.

Electrical feedthrough assemblies 108 that are used in, for example, body IMDs may potentially come in contact with bodily fluids. Thus, it is desirable that components of feedthrough assembly 108, such as terminal conductor 206, comprise bio-stable, non-corrosive materials. Terminal conductor 206 may comprise one or more of molybdenum, titanium, tantalum, platinum, iridium, zirconium, aluminum, stainless steel, nitrides of such metals, alloys of such metals, or one or more other bio-stable metals. In one example, terminal conductor 206 comprises molybdenum, which has a coefficient of thermal expansion (referred to as "CTE") similar to the CTE of an insulator 214 comprising glass. By substantially matching the CTE of insulator 214 with the CTE of terminal conductor 206, insulator 214 (e.g., glass) does not crack when it cools from an elevated temperature.

As discussed above, feedthrough assembly 108 comprises a sleeve 216 coupled to the internal portion 218 of terminal conductor 206. Sleeve 216 allows for, among other things, a more secure connection to be established between terminal conductor 206 and one or more components within encasement 110, such as an anode or cathode 202 of a battery. In particular, sleeve 216 allows for a more secure connection to be established between terminal conductor 206 and a conductive connection member 222 (e.g., a conductive ribbon), the latter of which links terminal conductor 206 to anode or cathode 202. Although not shown, anode and cathode 202 are typically separated by a separator, such as an ion-permeable separator.

Experimental tests have shown that pull-strengths of the connection between terminal conductor 206 and conductive connection member 222 greatly increase when a sleeve 216 is used in the connection scheme. For example, according to one test, the pull-strength of a terminal conductor 206/conductive connection member 222 connection using a sleeve 216 was found to be more than double that which was found when sleeve 216 was not used in the connection (i.e., when conductive connection member 222 was coupled directly to an outer surface of terminal conductor 206). Besides increased pull-strength, use of sleeve 216 may also advantageously help avoid connection failure or improve the mode by which connection failure occurs. As one example, use of sleeve 216 allows for force distribution on terminal conductor 206 in a manner that improves the fatigue resistance of the connection (i.e., the connection between terminal conductor 206 and conductive connection member 222).

Yet another advantage of sleeve 216 is that it can effectively change the material compositions of feedthrough assembly 108 components to be coupled. As one example, if terminal conductor 206 is composed of a first material and conductive connection member 222 is composed of a second material that is not easily weldable or otherwise couplable to the first material, sleeve 216 (composed of a material more compatible with the second material) may be crimped (or otherwise attached) to terminal conductor 206 thereby effectively changing the material composition of terminal conductor 206 (as far as conductive connection member 222 is concerned) to that of sleeve 216. Sleeve 216 may comprise stainless steel, aluminum, titanium, or any other material compatible with the particular battery chemistry.

FIGS. 3A-3C, 4A-4C, 5A-5C, 6A-6C, and 7A-7B illustrate various examples of sleeve 216 structures that may be used, such as to facilitate or strengthen a connection between a terminal conductor 206 (FIG. 2) and a conductive connection member 222 (FIG. 2). Sleeve 216 may be affixed to terminal conductor 206, such as via welding (see FIGS. 3A-3C), soldering (see FIGS. 3A-3C), brazing (see FIGS. 3A-3C), crimping (see FIGS. 4A-4C), or swaging (see FIGS. 5A-5C) techniques. In certain examples, sleeve 216 includes one or more notches 302, longitudinally-extending notches or voids 402, swage projections 502, flat portions 602, or introductory openings 702, such as to facilitate insertion of terminal conductor 206 within sleeve 216, attachment of sleeve 216 and terminal conductor 206, or positioning of sleeve 216 with respect to terminal conductor 206.

Sleeve 216 need not be specifically extruded during manufacture, but rather can be stock (off-the-shelf) tube or pipe, thereby reducing manufacturing costs (as compared with specifically extruded sleeves). In varying examples, a length 304 of sleeve 216 is sufficient to surround at least a portion of an internal portion 218 (FIG. 2) of terminal conductor 206. In one example, length 304 of sleeve 216 is 0.055 inches. In another example, length 304 of sleeve 216 is 0.070 inches. In varying examples, an inner diameter 306 of sleeve 216 is slightly larger than an outer diameter of terminal conductor 206. In one example, inner diameter 306 of sleeve 216 is 0.016 inches while an outer diameter 308 of sleeve 216 is 0.028 inches.

The example of sleeve 216 shown in FIGS. 3A-3C includes one or more notches 302, which may be used for the positioning of sleeve 216 relative to terminal conductor 206 or for connection between such components. In one example, notch 302 is used to (laser or resistance) weld, solder, or braze sleeve 216 to terminal conductor 206. In this example, notch 302 extends inward from a sleeve end face 310 and has a size of 0.016 inches×0.016 inches. In another example, notch 302 has a size of 0.012 inches×0.012 inches. Similarly, sleeve 216 may include at least one notch 302 extending inward from each sleeve end face 310.

The example of sleeve 216 shown in FIGS. 4A-4C includes a longitudinally-extending void 402, which may be used to couple sleeve 216 to terminal conductor 206, such as via crimping forces. Longitudinally-extending void 402 allows sleeve crimp faces 404 to move toward one another when a crimping force is applied to an outer surface of sleeve 216. As crimp faces 404 move closer to one another, inner diameter 306 of sleeve 216 is effectively reduced thereby increasing press-fitting forces experienced by an outer surface of terminal conductor 206 and inner surface of sleeve 216.

Figure 5A:
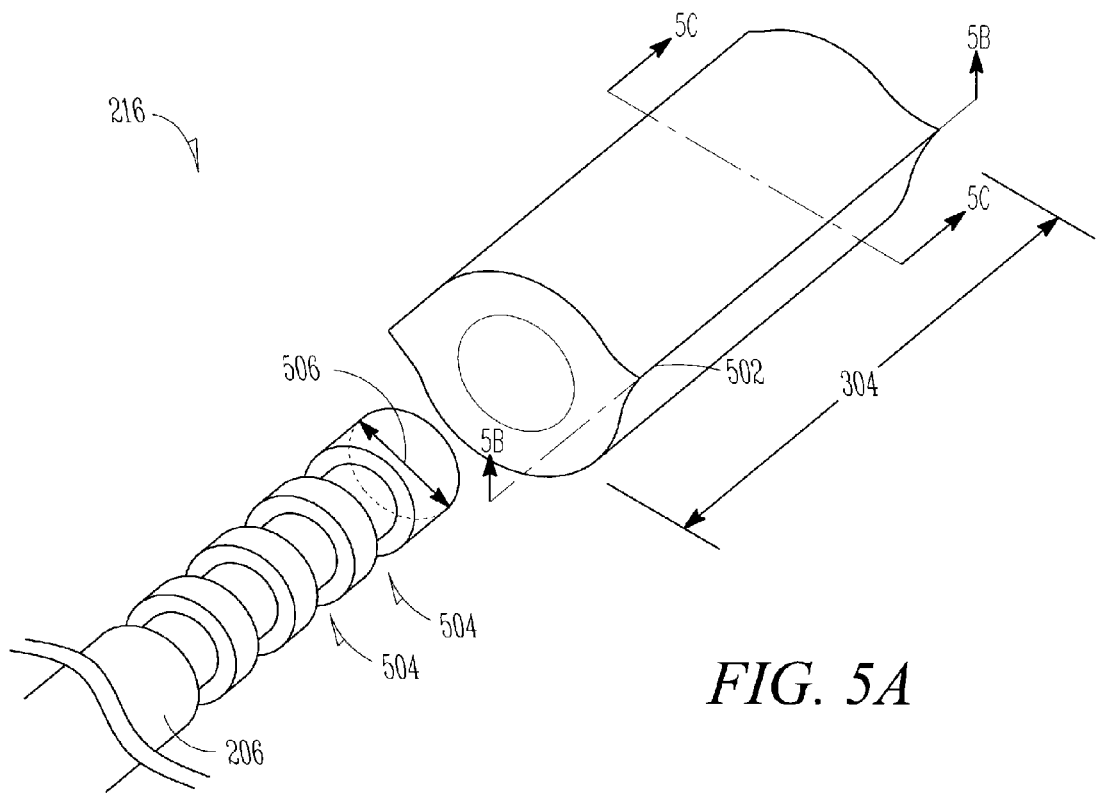
FIG. 5A illustrates an isometric view of another sleeve for use in a feedthrough assembly and a portion of a terminal conductor for coupling therewith.
Figure 5B:
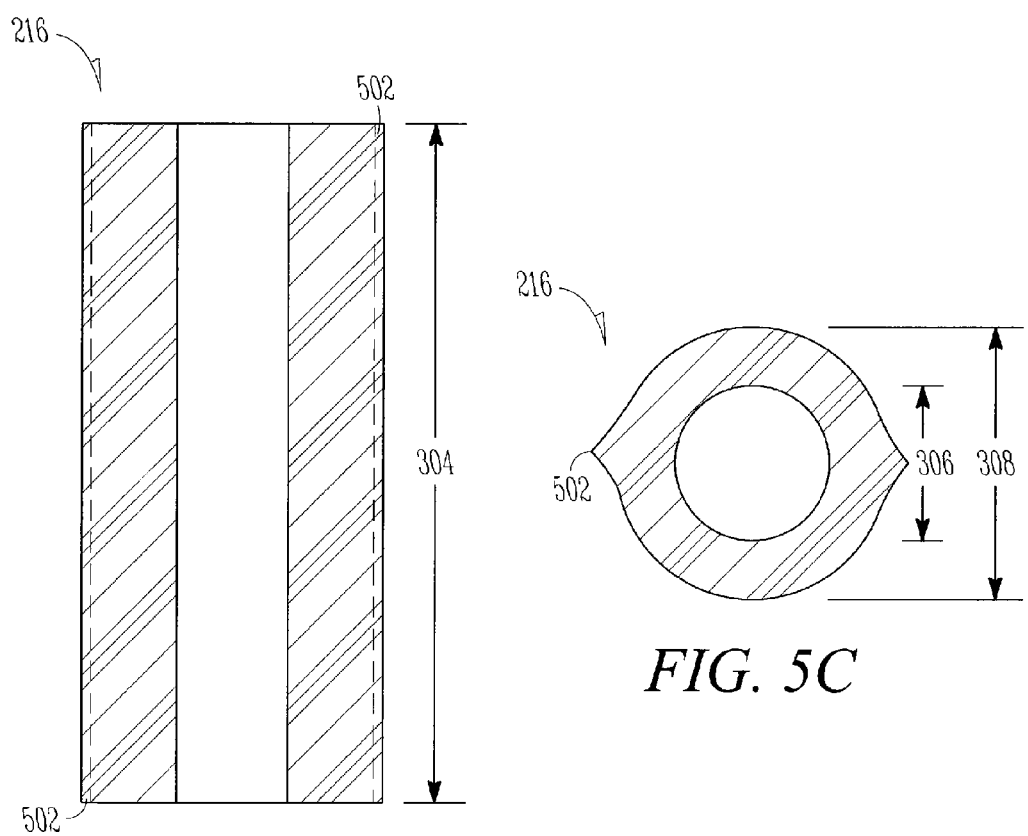
FIG. 5B illustrates a cross-sectional view of the sleeve of FIG. 5A along line 5B-5B.
Figure 5C:
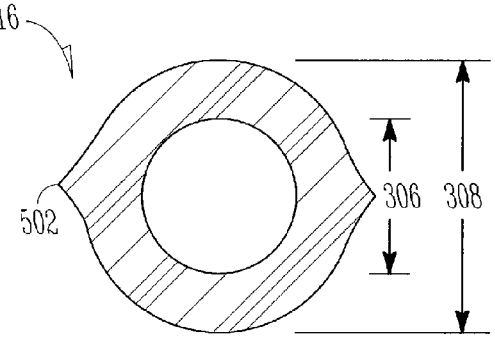
FIG. 5C illustrates a cross-sectional view of the sleeve of FIG. 5A along line 5C-5C.

FIGS. 5A-5C illustrate an example of sleeve 216 including one or more swage projections 502 and an internal portion 218 (FIG. 2) of a terminal conductor 206. In this example, internal portion 218 includes one or more grooves 504 into which portions of sleeve 216 may be deformed. In one example, after sleeve 216 is disposed over internal portion 218, the sleeve may be deformed, such as by rotary swaging (a metal forming process for the diametrical reduction of annular members, such as tubes). In this example, rotary swaging of sleeve 216 provides an inward force on swage projections 502 causing the shape of sleeve 216 to deform into grooves 504. As a result, sleeve 216 becomes affixed to terminal conductor 206.

FIGS. 6A-6C illustrate an example of sleeve 216 including a flat portion 602 extending the entire length 304 of the sleeve. Coupled to flat portion 602 is a first end of a conductive connection member 222. An opposing second end of connection member 222 may be attached to, for example, an anode or a cathode 202 of a battery. In this example, conductive connection member 222 comprises a stainless steel or other conductive ribbon. Flat portion 602 permits good surface contact with conductive ribbon 222, thereby allowing a solid weld or other coupling therebetween.

Figure 7A:
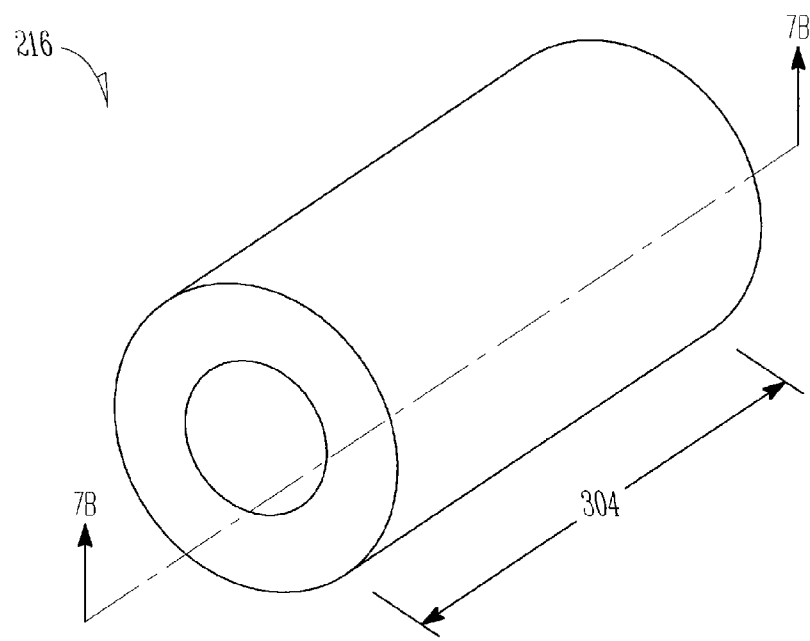
FIG. 7A illustrates an isometric view of yet another sleeve for use in a feedthrough assembly.
Figure 7B:
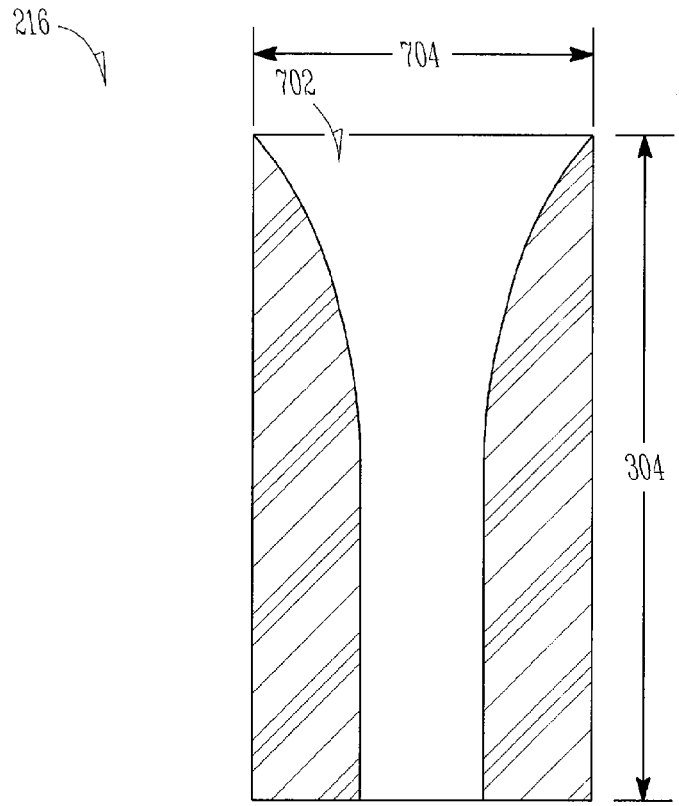
FIG. 7B illustrates a cross-sectional view along line 7B-7B of FIG. 7A.

The sleeve 216 in the example of FIGS. 7A-7B includes an introductory opening 702, which facilitates the insertion of a terminal conductor 206 (FIG. 2) into the sleeve. As shown in the example of FIG. 7B, an opening diameter 704 of introductory opening 702 is greater than a diameter 506 (FIG. 5A) of an internal portion 218 of terminal conductor 206. In this example, introductory opening 702 continuously narrows or otherwise tapers to a diameter slightly larger than diameter 506 but smaller than opening diameter 704, thereby guiding terminal conductor 206 within sleeve 216.

Figure 8:
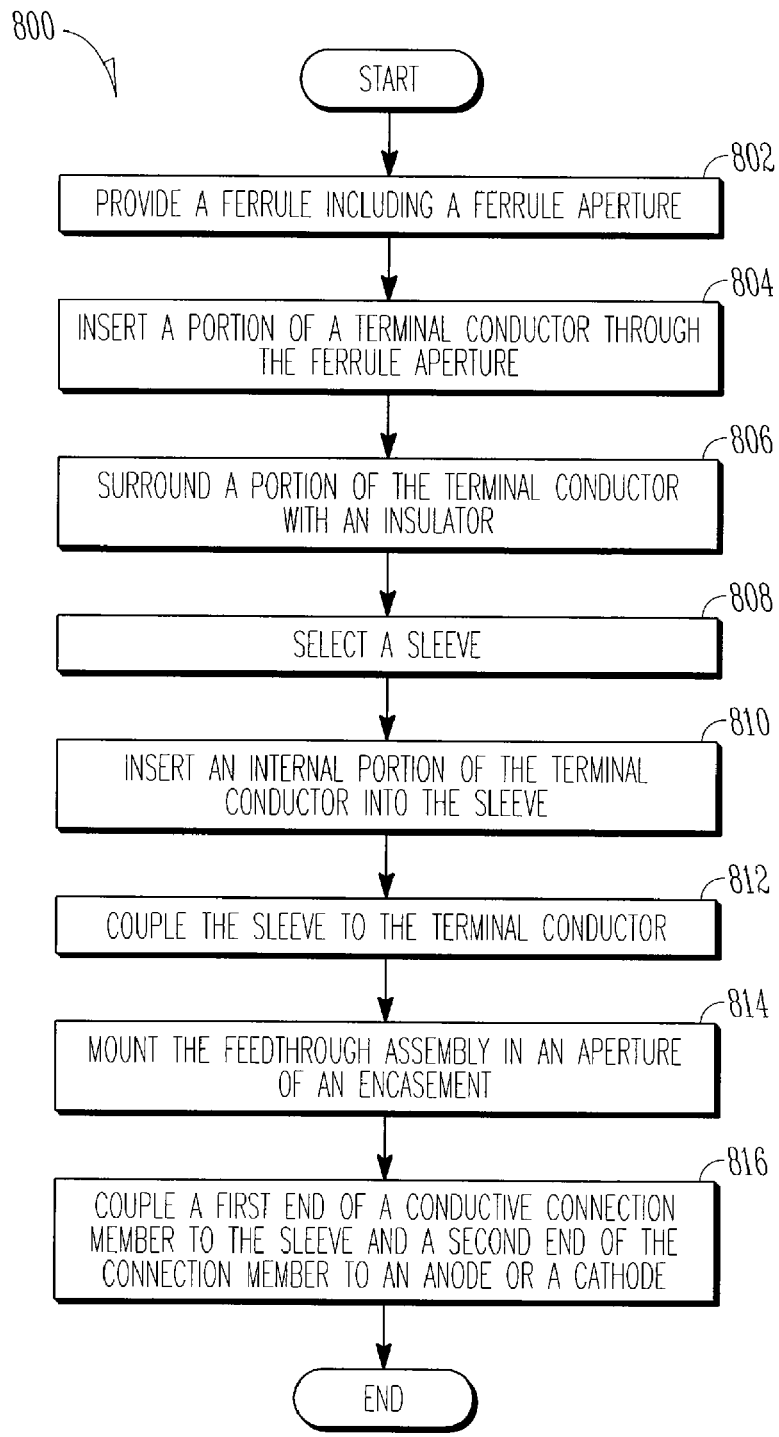
FIG. 8 illustrates a method of fabricating a feedthrough assembly comprising a sleeve.

FIG. 8 is a flow diagram illustrating a method 800 of fabricating a feedthrough assembly including a sleeve. At 802, a ferrule including a ferrule aperture is provided. At 804, a portion of a terminal conductor (e.g., a terminal pin) is inserted through the ferrule aperture such that when the ferrule is mounted in an aperture of an encasement (at 814), one end of the terminal conductor extends into an interior of the encasement and makes contact with a desired portion of the contents thereof, and the other end extends exteriorly of the encasement. At 806, a portion of the terminal conductor disposed within the ferrule aperture is surrounded by an insulator member or body (e.g., glass). In one example, surrounding the terminal conductor with the insulator includes sealably engaging the insulator with the terminal conductor to prevent any (e.g., electrolyte) leakage between such components.

At 808, a sleeve for attachment to the internal portion of the terminal conductor is selected. The sleeve may (but need not) contain notches, windows, chamfers, terminal conductor guidance cavities, or other voids or configurations, such as to facilitate overlapping, positioning, or attaching of the sleeve on or to the terminal conductor. At 810, the internal portion of the terminal conductor is inserted into the selected sleeve. In one example, insertion of the terminal conductor into the sleeve includes using a tapered introductory cavity (e.g., a funnel-shaped configuration) integrated with a sleeve first end.

At 812, the selected sleeve is (electrically) connected to the internal portion of the terminal conductor. In one example, connection of the sleeve to the terminal conductor includes (laser or resistance) welding, soldering, or brazing of the sleeve to the terminal conductor. In another example, connection of the sleeve to the terminal conductor includes crimping of the sleeve onto the terminal conductor. In yet another example, connection of the sleeve to the terminal conductor includes deformation (e.g., via rotary swaging) of the sleeve into one or more groove of the terminal conductor. In a further example, connection of the sleeve onto the terminal conductor includes heating the sleeve such that it expands, then placing the sleeve onto the terminal conductor, and finally allowing the sleeve to (compressively) cool onto the terminal conductor.

As discussed above, the feedthrough assembly is mountable in an aperture of an encasement, such as an electrical power source encasement, which occurs at 814. In one example, the feedthrough assembly is mounted in the aperture via welding, soldering, brazing, or through the use of an adhesive. At 816, a first end of the conductive connection member is coupled to the sleeve and a second end of the connection member is coupled to an anode or a cathode of an electrical power source battery. In one example, the conductive connection member includes a stainless steel ribbon which is welded to an internal portion of the sleeve on a first end and to the anode or cathode on a second end.

CONCLUSION

Feedthrough assemblies and methods for their manufacture are provided herein. Among other things, the present assemblies and methods provide a feedthrough assembly including a connection-facilitating sleeve. The sleeve increases the strength and fatigue resistance of interconnections between feedthrough components (e.g., the terminal conductor and conductive connection member). This enhances reliability of the feedthrough assembly and IMDs employing the same. In addition, use of the sleeve improves the manufacturability of feedthrough assemblies, as a greater (more robust) surface area is available for electrical coupling (e.g., welding, soldering, or brazing) between the conductive terminal and conductive connection member.

The present assemblies and methods are not limited to feedthroughs for batteries, but extend to other IMD or like applications where it is desired to penetrate a sealed encasement (i.e., a container), such as to provide electrical access to and from electrical components enclosed within. It will also be appreciated by those skilled in the art that while a number of specific dimensions or method orders are discussed above, the present assemblies can be made of any size (e.g., lengths, widths, or diameters) and may be fabricated in method orders other than those discussed.

It is to be understood that the above description is intended to be illustrative, and not restrictive. For example, the above-described embodiments (and/or aspects thereof) may be used in combination with each other. Many other embodiments will be apparent to those of skill in the art upon reviewing the above description. The scope of the present assemblies and methods should, therefore, be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract of the Disclosure is provided to comply with 37 C.F.R. § 1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, various features may be grouped together to streamline the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment.

Thus the following claims are hereby incorporated into the Detailed Description, with each claim standing on its own as a separate embodiment.

What is claimed is:

1. An implantable medical device comprising:
an encasement having at least one aperture therethrough;
an electrical power source in the encasement configured to provide power to electrical circuitry of the implantable medical device;
a feedthrough assembly at least partially positioned in the encasement aperture, the feedthrough assembly comprising,
a terminal conductor at least partially passing through the encasement aperture and extending from an internal portion disposed within the encasement to an external portion disposed outside the encasement, the terminal conductor including an outer surface;
an insulator disposed within at least a portion of the encasement aperture and surrounding at least a portion of the terminal conductor extending through the encasement aperture; and
a sleeve extending from a sleeve first end to a sleeve second end and having a sleeve intermediate portion therebetween, the sleeve including an inner surface engaged against the outer surface of the internal portion of the terminal conductor from near the sleeve first end to at least a midpoint of the sleeve substantially half way between the sleeve first end and the sleeve second end; and
a conductive connection member physically connected and electrically coupled to an outer surface of the sleeve, wherein the conductive connection member laterally approaches and laterally physically contacts the outer surface of the sleeve;
wherein the feedthrough assembly provides a conductive path extending between an interior of the encasement and a location outside of the encasement.

2. The implantable medical device as recited in claim 1, wherein the conductive connection member is electrically coupled to the sleeve at a member first end portion and electrically coupled to the electrical power source at a member second end portion.

3. The implantable medical device as recited in claim 2, wherein one or both of the sleeve or the conductive connection member comprise stainless steel.

4. The implantable medical device as recited in claim 2, wherein the outer surface of the sleeve includes a substantially flat portion to engage against a portion of a substantially flat conductive connection member.

5. The implantable medical device as recited in claim 4, wherein the substantially flat portion extends from near the sleeve first end to near the sleeve second end.

6. The implantable medical device as recited in claim 1, wherein the sleeve includes at least one weld or solder notch at one or both of the sleeve first end or the sleeve second end.

7. The implantable medical device as recited in claim 6, wherein the at least one weld or solder notch includes a dimensional length of at least 0.012 inches.

8. The implantable medical device as recited in claim 1, wherein the sleeve includes a longitudinally extending void; and comprising a crimp securing the sleeve to the outer surface of the terminal conductor, the crimp occurring by way of the longitudinally extending void.

9. The implantable medical device as recited in claim 1, wherein the internal portion of the terminal conductor includes one or more grooves extending inward from the outer surface thereof; and wherein the sleeve is configured to be deformable into the one or more grooves.

10. The implantable medical device as recited in claim 1, wherein the sleeve first end includes an introductory opening having a first diameter, the first diameter narrowing to a diameter larger than the outer diameter of the terminal conductor at or near the sleeve intermediate portion or the sleeve second end.

11. The implantable medical device as recited in claim 1, wherein the terminal conductor comprises molybdenum.

12. The implantable medical device as recited in claim 1, wherein a length of the sleeve as measured from the sleeve first end to the sleeve second end is at least about 0.055 inches.

13. The implantable medical device as recited in claim 1, wherein the inner surface of the sleeve is engaged against the outer surface of the terminal conductor from near the sleeve first end to near the sleeve second end.

14. The implantable medical device as recited in claim 1, wherein the sleeve is configured to laterally surround the internal portion of the terminal conductor from near the sleeve first end to near the sleeve second end.

15. The implantable medical device as recited in claim 1, wherein the sleeve comprises at least one of stainless steel, aluminum, or titanium.

16. The implantable medical device as recited in claim 1, wherein the terminal conductor comprises at least one of titanium, tantalum, platinum, iridium, zirconium, aluminum, or stainless steel.

17. The implantable medical device as recited in claim 1, wherein the terminal conductor comprises a material having a coefficient of the thermal expansion substantially the same as a coefficient of the thermal expansion of the insulator.

18. An implantable medical device comprising:
an encasement having at least one aperture therethrough;
an electrical power source in the encasement configured to power to electrical circuitry of the implantable medical device;
a feedthrough assembly at least partially positioned in the encasement aperture, the feedthrough assembly configured to provide a conductive path extending between an interior of the encasement and a location outside of the encasement, the feedthrough assembly comprising,
an insulator disposed within a portion of the encasement aperture;
a terminal conductor extending through the insulator, the terminal conductor having an internal portion disposed within the encasement and an external portion disposed outside of the encasement, the internal and external portions separated by a terminal conductor portion positioned within the insulator;
a sleeve extending from a sleeve first end to a sleeve second end, the sleeve including an inner surface directly coupled to an outer surface of the internal portion of the terminal conductor from near the sleeve first end, through a midpoint of the sleeve substantially half way between the sleeve first end and the sleeve second end, to near the sleeve second end; and
a conductive connection member physically connected and electrically coupled to an outer surface of the sleeve, wherein the conductive connection member laterally approaches and laterally physically contacts the outer surface of the sleeve.

19. The implantable medical device as recited in claim 18, comprising a ferrule in contact with the encasement on an outer ferrule surface and in contact with the insulator on an inner ferrule surface.

20. The implantable medical device as recited in claim 18, wherein the sleeve includes at least one notch extending from one or both of the sleeve first end or the sleeve second end.

21. The implantable medical device as recited in claim 20, comprising a weld or solder configured to secure the sleeve to the outer surface of the terminal conductor; and wherein the weld or solder is disposed adjacent the at least one notch.

22. The implantable medical device as recited in claim 18, wherein the sleeve includes a longitudinally extending void; and comprising a crimp securing the sleeve to the outer surface of the terminal conductor, the crimp occurring by way of the longitudinally extending void.

23. The implantable medical device as recited in claim 18, wherein the internal portion of the terminal conductor includes one or more grooves extending inward from the outer surface thereof; and wherein the sleeve is configured to be deformed into the one or more grooves.

24. The implantable medical device as recited in claim 18, wherein the outer surface of the sleeve is electrically coupled to one of a cathode assembly or an anode assembly of the electrical power source; and the inner surface of the sleeve is electrically engaged with the internal portion of the terminal conductor.

25. The implantable medical device as recited in claim 18, wherein the conductive connection member includes a member first end electrically coupled to the outer surface of the sleeve and a member second end electrically coupled to one of the cathode assembly or the anode assembly.

26. The implantable medical device as recited in claim 25, wherein the outer surface of the sleeve is configured to mate with a portion of the conductive connection member.

27. The implantable medical device as recited in claim 25, comprising a weld between the outer surface of the sleeve and the conductive connection member.

* * * * *

UNITED STATES PATENT AND TRADEMARK OFFICE
CERTIFICATE OF CORRECTION

PATENT NO. : 7,561,917 B2  Page 1 of 1
APPLICATION NO. : 11/277213
DATED : July 14, 2009
INVENTOR(S) : Thomas J. Wegrzyn et al.

It is certified that error appears in the above-identified patent and that said Letters Patent is hereby corrected as shown below:

In column 8, line 49, in Claim 4, after "portion" insert -- configured --.

In column 9, line 32, in Claim 17, after "of" delete "the".

In column 9, line 33, in Claim 17, after "of" delete "the".

Signed and Sealed this

Sixth Day of October, 2009

David J. Kappos
*Director of the United States Patent and Trademark Office*